US007298817B2

(12) United States Patent
Chen et al.

(10) Patent No.: US 7,298,817 B2
(45) Date of Patent: Nov. 20, 2007

(54) PORTABLE AND ON-LINE ARSENIC ANALYZER FOR DRINKING WATER (75) Inventors: Zewu Chen, Schenectady, NY (US); Walter M. Gibson, Voorheesville, NY (US)

(73) Assignee: X-ray Optical Systems, Inc., East Greenbush, NY (US)

( * ) Notice: Subject to any disclaimer, the term of this patent is extended or adjusted under 35 U.S.C. 154(b) by 45 days.

(21) Appl. No.: 11/000,535

(22) Filed: Nov. 30, 2004

(65) Prior Publication Data
US 2005/0157843 A1 Jul. 21, 2005

Related U.S. Application Data (60) Provisional application No. 60/526,003, filed on Dec. 1, 2003.

(51) Int. Cl.
*G01N 23/223* (2006.01)
(52) U.S. Cl. .......................................... 378/47; 378/44
(58) Field of Classification Search ............ 378/42–50
See application file for complete search history.

(56) References Cited

U.S. PATENT DOCUMENTS

| 4,460,274 | A | * | 7/1984 | Schumann et al. ......... 356/318 |
| 5,014,287 | A | * | 5/1991 | Thornton et al. ............. 378/45 |
| 6,285,734 | B1 | * | 9/2001 | von Alfthan .................. 378/46 |
| 6,310,935 | B1 | * | 10/2001 | Kuwabara .................... 378/49 |
| 6,697,454 | B1 | * | 2/2004 | Nicolich et al. .............. 378/85 |
| 2004/0240606 | A1 | * | 12/2004 | Laurila et al. ................ 378/45 |

OTHER PUBLICATIONS

S. Raj et al., "Valence Electronic Structure of Mn in Undoped and Doped Lanthanum Manganites from Relative K X-Ray Intensity Studies", Nuclear Instruments and Methods in Physics Research, Section—B: Beam Interactions with Materials and Atoms, , Elsevier, Amsterdam, NL, vol. 174, No. 3, pp. 344-350 (Apr. 2001).
H. Ida et al., "Analysis of Wrapped of Cased Object by a Hand-Held X-Ray Fluorescence Spectrometer", Forensic Science International, Elsevier Scientific Publishers Ireland, Ltd., IE, vol. 151, No. 2-3, pp. 267-272, (Jul. 16, 2005).
P.J. Custodio et al., "Direct Analysis of Human Blood (Mothers and Newborns) by Energy Dispersive X-Ray Fluorescence", Journal of Trace Elements in Medicine and Biology, vol. 19, pp. 151-158 (Dec. 2, 2005).

* cited by examiner

*Primary Examiner*—Hoon Song
(74) *Attorney, Agent, or Firm*—Jeffrey Klembczyk, Esq.; Kevin P. Radigan, Esq.; Heslin Rothenberg Farley & Mesiti, P.C.

(57) ABSTRACT

An x-ray fluorescence technique for detecting the level of arsenic in a sample of water or body fluid. Arsenic and lead are expected to fluoresce in a first energy band and lead is expected to also fluoresce separately in a second energy band. An excitation path directs x-rays toward the sample; a first detection path detects x-ray fluorescence of the first energy band from the sample; and a second detection path detects x-ray fluorescence of the second energy band from the sample. The level of arsenic can be obtained by analyzing the x-ray fluorescence from both detection paths, and using a constant which relates the level of lead in the second energy band to the level of lead in the first energy band. The excitation path and each detection path may each include a monochromating optic to transmit the desired x-ray energy band, e.g., a doubly curved optic.

27 Claims, 7 Drawing Sheets fig. 1 fig. 2 fig. 3a fig. 3b fig. 3c fig. 4 fig. 5 fig. 6A fig. 6B fig. 7A fig. 7B

PORTABLE AND ON-LINE ARSENIC ANALYZER FOR DRINKING WATER

Priority Information

This application derives priority from U.S. Provisional Application No. 60/526,003, filed Dec. 1, 2003, entitled PORTABLE AND ON-LINE ARSENIC ANALYZER FOR DRINKING WATER. This Provisional Application is incorporated herein by reference in its entirety.

TECHNICAL FIELD

This invention relates in general to testing samples for contamination from, e.g., transition and/or heavy metals. More particularly this invention relates to a technique (method and apparatus) for using monochromatic x-ray fluorescence for detecting metals such as arsenic and lead in samples such as drinking water.

BACKGROUND OF THE INVENTION

Arsenic is known to be associated with both cancer and non-cancer health problems. This has recently been the focus of public attention due to the almost epidemic health problems of millions of people in Bangladesh and West Bengal, India, caused by As-contaminated groundwater (Kinniburgh, D. G. and Smedley, P. L., "Arsenic Contamination of Groundwater in Bangladesh, Vol. 2: Final Report," BGS Technical Report WC/00/19, British Geological Survey, Keyworth, 2001; http://bgs.ac.uk/arsenic/bangladesh/reports.htm; Kinniburgh, D. G., Smedley, P. L., Davies, J., Milne, C. J., Gaus, I., Trafford, J. M., Burden, S., Ihtishamul Huq, S. M., Ahmad, N., and Ahmak, K. N., "The scale and causes of the groundwater arsenic problem in Bangladesh," in Arsenic in Ground Water, Welch and Stollenwerk, eds, Kluwer, Boston, 2003 p 211—incorporated herein by reference in their entirety). Chronic exposure to As via drinking water causes skin, lung, bladder, prostate, and kidney cancer (National Research Council 1999; "Arsenic in Drinking Water" Washington, D.C., National Academy Press—incorporated herein by reference in its entirety). Recent evidence suggests that increased chronic exposure to As might also be associated with an increased risk of high blood pressure and diabetes.

To protect people against the effects of long-term exposure to As, the World Health Organization has set a provisional guideline concentration for drinking water of 10 ug/L (ppb) (WHO, "Guidelines for drinking water quality" 2nd Ed, Volume I Recommendations: World Health Organization, 1993, p 188—incorporated herein by reference in its entirety). The US EPA has proposed lowering the maximum contaminant level for As in drinking water from 50 ug/L to 10 ug/L (ppb). High concentrations of As tend to be found more in ground water than in surface water. Since more groundwater sources are used for public drinking water supplies or private wells, the As contamination in drinking water has become a serious worldwide issue. Ground water with a serious contaminant level of As can be found in many countries, including Bangladesh, Western India, Taiwan, Mongolia, Vietnam, Argentina, Chile, Mexico, and the United States (Matschullat, J., "Arsenic in the geosphere—a review", Sci. Total, Environ., 249, 297-312, 2000—incorporated herein by reference in its entirety).

In the United States, half the population relies on ground water for drinking. There are many areas with a widespread high As concentration in ground water (Welch, A. H., Helsel, D. R., Focazio, M. J., and Watkins, S. A., "Arsenic in ground water supplies of the United States", in Chappell, W. R., Abernathy, C. O. and Calderon, R. L., eds., Arsenic Exposure and Health Effects, Elsevier, Amsterdam, 1999, p. 416, incorporated herein by reference in its entirety). Arsenic concentrations up to 12 ppm (12,000 ppb) have been measured in ground water from a sandstone aquifer in the Fox River Valley in eastern Wisconsin. About 21% of private water supply wells in Outagamie and Winnebago counties in Wisconsin exceed 10 ppb and 4% of the wells exceed 50 ppb. In southeastern Michigan, about 70% of ground water samples taken from more than 100 wells, have an arsenic content of more than 10 ppb, with measured levels up to 220 ppb. In the Albuquerque Basin of central new Mexico, where more than 700,000 residents rely almost exclusively on ground water for drinking water supplies, the arsenic concentration in ground water underlying the basin has been detected in excess of 600 ppb, and concentrations exceeding 20 ppb are present across larger areas (Welch, A. H., Westjohn, D. B., Helsel, D. R., and Wanty, R. B., "Arsenic in ground water of the United States: Occurrence and geochemistry", Ground Water, 38 (no. 4), 589-604, 2000—incorporated herein by reference in its entirety).

Reliable measurement of metal traces at the few ppb level is a challenging task. There are primarily two categories of methods for ultra-trace analysis; namely atomic absorption/emission spectroscopy (AAS, or AES) and inductively coupled plasma (ICP) based methods. In the AAS methods, a small sample (uL level) is placed into a high temperature graphite furnace where it is heated to the gas phase in the presence of a carrier gas. The attenuation of light of selected wavelengths is then measured to determine the amount of As. This is a very sensitive method and the detection limits are in the sub ppb range. However, the dynamic range of the technique is limited to 1-50 ppb and high concentration samples need to be diluted. Other disadvantages of AAS include high power consumption (~6 kW) and requirement of inert ambient gas for the furnace. ICP based methods, including atomic emission spectrometry (ICP-AES) and mass spectrometry (ICP-MS), are powerful ultra-trace elemental analysis methods. The detection limit can go down to the part per trillion (ppt) range and these techniques have a very large dynamic range. However, ICP based methods are even more sophisticated than AAS methods. They require high vacuum, high power (~6 kW), and plasma gas. Due to their degree of sophistication and requirement of extensive facilities, AAS and ICP methods are laboratory based methods and have great difficulty being used for field or on-line applications.

Other trace analysis techniques include electrochemical methods, such as potentiometric stripping analysis (PSA). These methods are based on electrochemical processes between electrodes and electrolyte solutions. In PSA measurements a reference is needed, as well as sophisticated sample preparation. They typically show poor reproducibility and are sensitive to the detailed chemical makeup of the sample. Consequently, electrochemical methods are not extensively used for laboratory analysis. Repeatability and reproducibility of these methods are major issues and make them difficult for field and on-line applications.

SUMMARY OF THE INVENTION

The shortcomings of the prior art are overcome and additional advantages are provided by the present invention, which includes an x-ray fluorescence technique (system, method) for detecting the level of arsenic in a sample of water or body fluid. Arsenic and lead are expected to fluoresce in a first energy band and lead is expected to also fluoresce separately in a second energy band. An excitation path directs x-rays toward the sample; a first detection path detects x-ray fluorescence of the first energy band from the sample; and a second detection path detects x-ray fluorescence of the second energy band from the sample.

The level of arsenic can be obtained by analyzing the x-ray fluorescence from both detection paths, and using a constant which relates the level of lead in the second energy band to the level of lead in the first energy band thereby providing the level of arsenic in the first energy band.

One or both of the detection paths may include a monochromating optic adapted to transmit energy from the respective energy band; and the monochromating optic may be a doubly curved crystal optic.

The excitation path may include an excitation optic for focusing the x-rays onto the sample; and the excitation optic may be a monochromating optic adapted to transmit x-rays of both the first and second energy bands.

The sample may be a continuous stream or a static sample.

Elements other than arsenic and lead, in samples other than water, may be the subject of the x-ray fluorescence techniques of the present invention.

If a-priori knowledge is available about the level of other elements (e.g., lead) if any is present in the first energy band, the invention may exclude the second detection path.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter regarded as the invention is particularly pointed out and distinctly claimed in the claims at the conclusion of the specification. The foregoing and other objects, features, and advantages of the invention are apparent from the following detailed description taken in conjunction with the accompanying drawings in which:

BEST MODE FOR CARRYING OUT THE INVENTION

X-ray fluorescence analysis (XRF) is a direct elemental-analysis technique requiring little or no sample preparation. It has proven to be one of the most reliable and robust analytical methods for many industrial applications. In fact, there are several types of portable or handheld XRF instruments for field applications. However, for measurement of As in ground water there are two major issues for the current portable XRF methods. The first one is sensitivity; the best sensitivity of portable XRF devices is only about 10 ppm. Even with a state of the art XRF system in the laboratory, equipped with high power (4 kw) x-ray tube and wavelength dispersive system, the detection limit for As in water would be barely 10 ppb. The second issue is that many portable XRF devices are based on radioactive sources. Radioactive sources themselves are a concern for environmental safety. Recently, handheld XRF devices with miniature x-ray tubes have been developed, but the sensitivities for these instruments are in the high (>100) ppm level.

In this invention, a novel x-ray fluorescence (XRF) method, Wavelength Dispersive Monochromatic XRF analysis based on doubly curved crystal (DCC) x-ray optics, measures As at low ppb or sub ppb levels for both field testing and on-line applications. The detection limits are drastically improved by combining the advantages of both monochromatic excitation and wavelength dispersive spectrometry. Monochromatic excitation using a low power tube and an efficient and compact Arsenic WD spectrometer is only made possible by the use of efficient x-ray optics.

Figure 1:
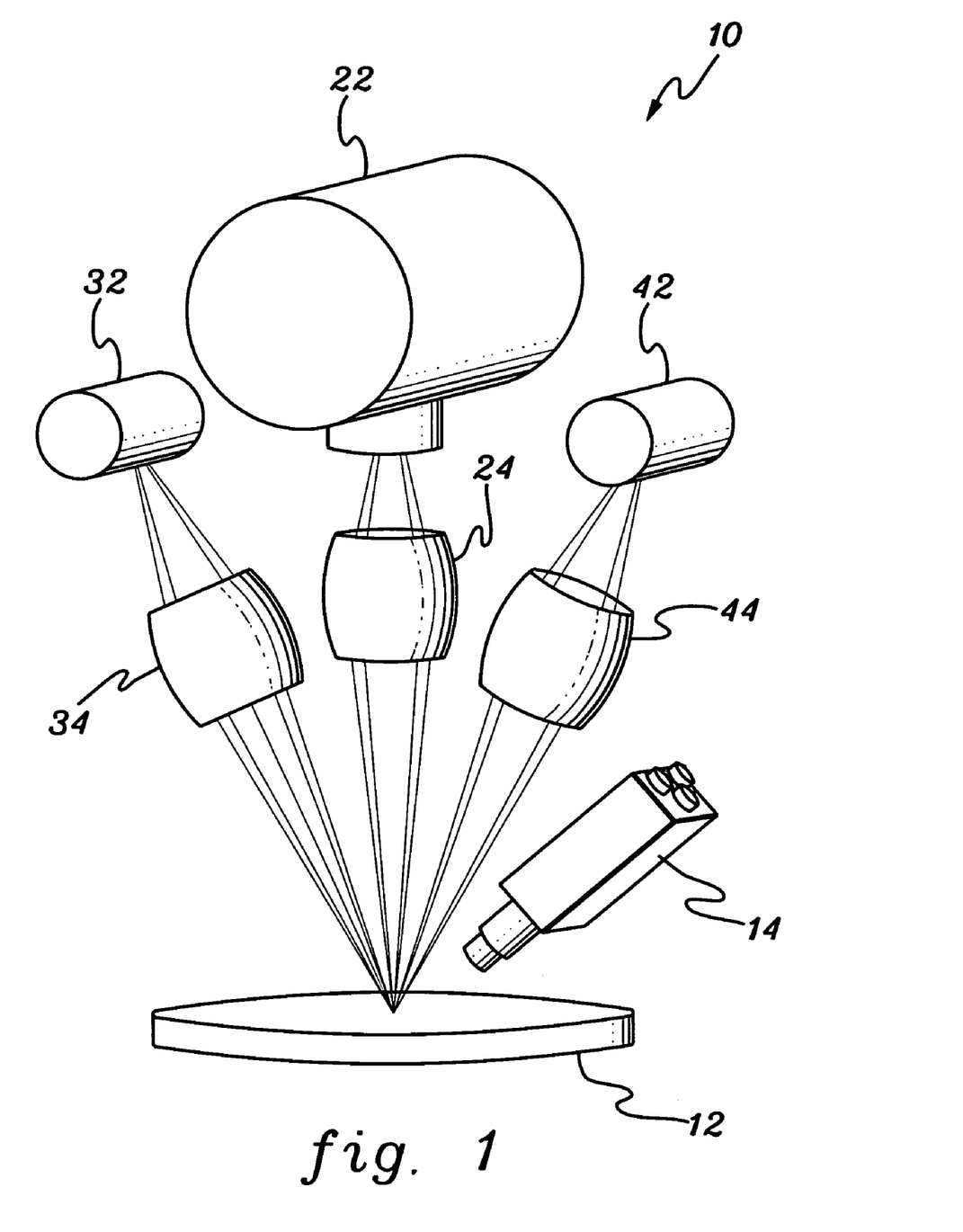
FIG. 1 depicts a schematic diagram, in accordance with an aspect of the present invention, of a system for measuring As and Pb by wavelength dispersive, monochromatic XRF analysis, with an excitation DCC, a collection DCC for As K$\alpha$ & Pb L$\alpha$ photons, and another collection DCC for Pb K$\beta$ photons.
Figure 2:
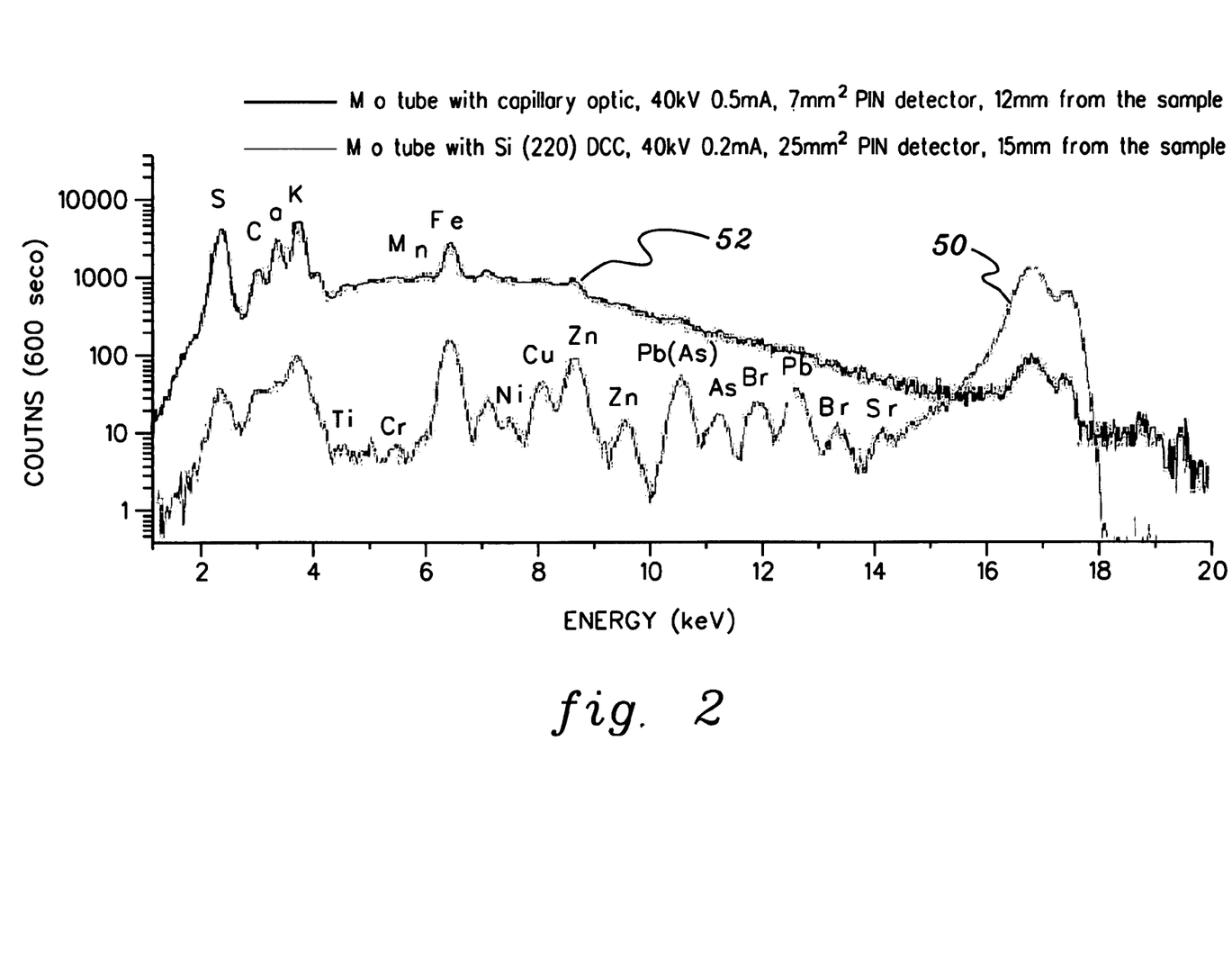
FIG. 2 is a comparison of energy dispersive spectra of an air particulate sample with monochromatic DCC optic excitation and polychromatic polycapillary optic excitation.

The WD-MXRF method/system 10 in accordance with one aspect of the present invention for measuring As and Pb is shown schematically in FIG. 1. Three advanced monochromating (e.g., doubly curved crystal—DCC) optics 24, 34, 44 are disclosed for this WD-MXRF method. The first DCC 24, the excitation DCC, is used to form an intense monochromatic beam, a Mo K$\alpha$ beam, from an exemplary low power Mo anode x-ray source 22 for exciting As and Pb atoms in the sample 12. For liquid samples, a standard plastic XRF cup with a mylar film can be used. Monochromatic excitation eliminates the dominating bremsstrahlung background present in conventional XRF instruments with polychromatic excitation. This improves the signal to background ratio (S/B) by more than two orders of magnitude. This improvement is shown in FIG. 2 by the comparison of energy dispersive spectra between the monochromatic 50 and polychromatic 52 excitation.

The second DCC 34 with an exemplary energy bandwidth of about 20 eV is designed for collecting (e.g., from a first energy band where both As and Pb are expected to fluoresce) 10.54 keV photons to an x-ray counter, where the intensity of the As K$\alpha$ line (10.543 keV) plus the Pb L$\alpha_1$ line (10.549 keV) are determined. Therefore both As K$\alpha$ characteristic photons and Pb L$\alpha$ photons are collected by this DCC. The third DCC 44 (bandwidth about 20 eV), is designed to select (e.g., from a second energy band where only Pb is expected to fluoresce) 12.61 keV photons, where the intensity of the Pb L$\beta_1$ line with no As interference, is measured. The intensity ratio of Pb L$\alpha_1$ to Pb L$\beta_1$ is a fundamental constant, 2.0, so both the As and Pb concentration can be determined from the intensities using fundamental parameters. The lead contamination in ground water is usually insignificant so the correction to the measured Arsenic K$\alpha$ line will not usually be important. On the other hand, this analyzer can be used to measure the presence of Pb which is an important toxic contaminant if present.

As an optional feature, a small PIN energy dispersive (ED) solid state detector 14 can be added for multi-element analysis at low ppm and sub ppm levels.

In one embodiment, if pre-testing results in a-priori information indicating the level of lead or other element in the first energy band, if any, then the analyzer can operate with one detection path only, on the first energy band to detect Arsenic—knowing a-priori that there is no interfering element present, or that a known level of an interfering element is present.

Though DCC excitation is disclosed here, any type of monochromators can be used. Exemplary doubly curved crystal optics are disclosed in X-Ray Optical Systems, Inc. U.S. Pat. Nos. 6,285,506 and 6,317,483; and U.S. Provisional Application Ser. Nos. 60/400,809 (filed Aug. 2, 2002 entitled AN OPTICAL DEVICE FOR DIRECTING X-RAYS HAVING A PLURALITY OF OPTICAL CRYSTALS, and perfected as PCT Application PCT/US3/23412)—all of which are incorporated by reference herein in their entirety. Singly curved crystals, multi-layer optics and pin-hole or slot collimating optics may also be used.

The optics may provide beam gain, as well as general beam control. Also, monochromating optical elements may be desirable in the excitation and/or emission paths for narrowing the radiation bands depending on the sample's characteristics—along with polycapillary optics for beam focusing—such as monocapillary optics (see, e.g., X-Ray Optical Systems, Inc. U.S. Pat. No. 5,747,821 all of which is incorporated by reference herein in its entirety); and polycapillary optics (see, e.g., X-Ray Optical Systems, Inc. U.S. Pat. Nos. 5,192,869; 5,175,755; 5,497,008; 5,745,547; 5,570,408; and 5,604,353;—all of which are incorporated by reference herein in their entirety).

Optic/source combinations are also useable such as those disclosed in X-Ray Optical Systems, Inc. U.S. Provisional Application Ser. Nos. 60/398,968 (filed Jul. 26, 2002 entitled METHOD AND DEVICE FOR COOLING AND ELECTRICALLY-INSULATING A HIGH-VOLTAGE, HEAT-GENERATING COMPONENT, and perfected as PCT Application PCT/US02/38803); 60/398,965 (filed Jul. 26, 2002 entitled X-RAY SOURCE ASSEMBLY HAVING ENHANCED OUTPUT STABILITY, and perfected as PCT Application PCT/US02/38493) and 60/492,353 (filed Aug. 4, 2003 entitled X-RAY SOURCE ASSEMBLY HAVING ENHANCED OUTPUT STABILITY USING TUBE POWER ADJUSTMENTS AND REMOTE CALIBRATION, and perfected as PCT Application PCT/US04/25113)—all of which are incorporated by reference herein in their entirety.

There are several important aspects of the exemplary optical configuration of system 10 of FIG. 1. First, all three DCCs have novel geometries that can provide more than 100× intensity improvement compared to conventional singly curved crystal WD analyzers, and 3× to 10× improvement compared to a doubly curved Johann type geometry ("Doubly curved crystal (DCC) X-ray optics and applications", Powder Diffraction 17 (2), pp 99-103—incorporated herein by reference in its entirety).

They may have a potential 360° revolving structure to achieve a large collection solid angle. Their detailed geometries are described elsewhere herein. A large collection angle is the key to achieving high instrument sensitivity and makes the use of a low-power x-ray tube possible. Also the excitation DCC not only provides an intense monochromatic beam (>$10^9$ photons/s), but also focuses x-rays down to ~200 μm spot onto the sample. This allows the fluorescent x-ray signal to emanate from a small spot so that the collection DCC optics can be used efficiently. These aspects of the x-ray optical system provide the physical basis for sub ppb detection limits even with the use of a low-power x-ray source, as indicated by preliminary data discussed below. It is important to note that although disclosed in the present case for water samples, this analyzing system can be used for other solid or liquid samples as well. This is because no sample preparation is necessary except for possible pulverization of non-homogeneous samples. This can be crucial in the field study of both sources and the consequences of ground water contamination. Furthermore, the focused excitation beam means that a straightforward sample scanning system could allow mapping of As (or Pb) distributions in non-homogeneous samples with spatial resolution of 200-300 μm.

Other important aspects of the WD-MXRF system are as follows. First, there is no sample preparation, making it a direct measurement. Second, the detection of As and Pb is not interfered with by the presence of other elements present at high concentration levels because of the narrow energy window of the collection DCC optics. These two important benefits are the basis for achieving excellent repeatability and reproducibility. All other ultra-trace techniques, such as ICP or AAS/AES methods, require extensive sample preparation and are sensitive to interference, especially for "dirty samples" with high concentration levels of other elements. Third, the proposed system can have a linear response from <1 ppb to >1000 ppm at a single setting, providing more than 6 decades of dynamic range. With lower power settings and self-absorption corrections, the concentration can even go up to percentage levels. Finally, this is a compact WD-MXRF analyzer with low power (<100 W total) and no moving parts. This difference compared to conventional high power WDXRF systems, make it suitable for in-field and on-line applications. The detailed configurations for in-field testing and on-line measurements are described elsewhere herein.

Application:

The capability of field testing with no sample preparation is invaluable for many environmental applications. The As/Pb analyzer can have a great impact to address the global As issue in drinking water. It can generate large economic as well as health benefits, if most of the analysis can be done in the field or in local laboratories to which water samples from private wells can be taken. It can also provide a monitoring tool for water suppliers for quality control. Also the As/Pb analyzer is much less expensive than the cost of purchasing and operating ICP and AAS instruments (estimated at about ⅕-1/10 of ICP-MS instruments). Furthermore, the instrument can be operated in relatively uncontrolled conditions (temperature, humidity, etc.) by minimally trained personnel, as already demonstrated by existing sulfur analysis instruments. Also, the WD-MXRF technique can be applied to other environmental applications. As noted previously, samples can be measured directly and can be virtually any solid or liquid. Different collection DCCs can also be configured to detect other environmentally important elements, such as Hg, Cd and Cr. A modular design approach could allow easy switching of DCC optics for different applications. These applications might include soil, plant, and food contamination analysis.

Also, the WD-MXRF technique also has great potential for clinical applications. Trace metals in blood, urine, and body fluids are of great concern for human health. Detecting trace metals, such as Pb, Hg, As, Tl, and Se, by current techniques is expensive and time-consuming. A simple bench-top analyzer in a clinic or hospital could be a great benefit and cost effective and could address many issues confronted by current analytical techniques.

Background R&D Support:

Crystal x-ray optics and their applications on elemental analysis, x-ray diffraction, and other x-ray spectroscopies are presented.

Advanced Doubly Curved Crystal (DCC) Optics

Doubly curved crystal optics were known to be useful for focusing and monochromatizing x-rays from small x-ray sources for decades. But their application was been hindered due to the great difficulty in controlled fabrication. Advanced DCC optics, which can provide a 5 to 50× improvement compared to the early DCC geometry, have been invented and successfully fabricated. These geometries include fully revolving DCC optics, asymmetrically cut DCC optics, and logarithmic DCC optics, as disclosed in the above-incorporated U.S patents and patent applications.

Applications of Doubly Curved Crystal Optics

The availability of DCC optics has opened the door for conceiving many novel x-ray techniques for a variety of applications. Several new methods based on DCC optics have newly been proposed: X-ray absorption near edge spectroscopy (XANES) using DCC for oxidation state analysis, focused beam total-reflection XRF (TXRF) for extreme ultra-trace analysis, and fixed channel WDXRF using monochromatic excitation.

Sulfur Analyzer for Petroleum Industry

Based on related WD-MXRF concepts, a sulfur analyzer has been successfully developed by XOS using doubly curved crystal optics. Sulfur in fuel is a serious environmental concern and the sulfur concentration in diesel fuel will be regulated down to 15 ppm by 2006. There is a great need in the petroleum industry for a reliable on-line or in-the-field method to measure sulfur. With extensive R&D effort, detection limits of 200 ppb have been achieved (http://www.xos.com/sulfuranalyzer.htm). And the WD-XRF method was demonstrated to be the most reproducible of currently available techniques. It should be noted that the low energy of sulfur Kα x rays make the measurement of sulfur much more difficult and less sensitive than for As or other heavy metal contaminants. Indeed, direct scaling of the sulfur measurements to account for window absorption, collection efficiency, and detection and fluorescence yield factors allow a reliable estimation of sub ppb measurements for As.

Figure 4:
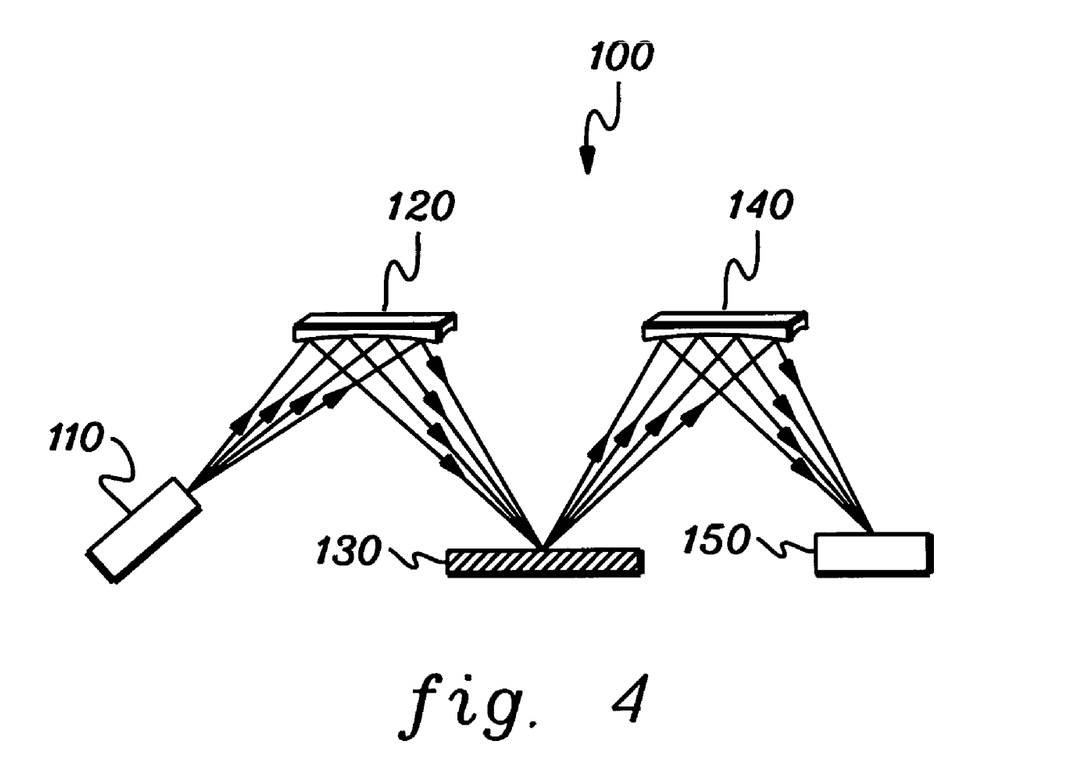
FIG. 4 depicts a sulfur analyzer based on the WD-MXRF method including a sample, excitation DCC, collection DCC, x-ray tube, and proportional counter.

This sulfur analysis technique is discussed further below in connection with FIG. 4.

Detection Limits of ICP Based Methods

Inductively coupled plasma atomic emission spectroscopy (ICP-AES) (Ure, A. M., "Methods of analysis for heavy metals in soils", in Heavy Metals in Soils, B. J. Alloway, ed. (Blackie, Glasgow, 1990) pp. 40-80—incorporated herein by reference in its entirety) and inductively coupled plasma mass spectrometry (ICP-MS) (Bortoli, P., Gerotto, M., Marchiori, M., Palonta, R., Troncon, A., "Applications of inductively coupled plasma mass spectrometry to the early detection of potentially toxic elements", Michrochem J., 46, 159-166 (1992)—incorporated herein by reference in its entirety) techniques are the most widely used ultra-trace methods for laboratory based environmental analysis. It is not suggested that these techniques will be replaced by WD-XRF instruments. In general ICP-MS has higher sensitivity and also can give isotopic ratio information. The detection limits for As using ICP-MS can be as low as 0.01 ppb (Slavin, "Comparison of Atomic-Spectroscopic Analytical Techniques", Spectroscopy, 6, pp 16-21). ICP-AES typically has poorer detecting limits than ICP-MS and its detection limits for As are at sub ppb level. ICP based methods are well established laboratory techniques, but these methods can not be used for field and on-line application due to their high degree of operation sophistication and extensive facilities required as well as cost and size.

Background Sensitivity Analysis:

Intense Monochromatic Beams with Low Power Tubes

As discussed above, several types of DCC optics with a larger collection solid angle than Johann type DCC optics have been developed. The improvement of the collection solid angle comes from the combination of asymmetrically cut crystals with symmetrical crystals to approximate the intrinsically more efficient Johansson geometry. Using this type of DCC with a low power x-ray source, highly intense monochromatic focused beams have been obtained for monochromatic excitation. Table I shows Cr Kα beam and Mo Kα beam parameters using 75 w x-ray tubes.

TABLE I

Intensity of Cr Kα and Mo Kα beams and related parameters of DCCs

| Optics and source | Solid angle | Reflectivity (%) | Effective solid angle (solid angle × Reflectivity) | Intensity (photons/s) | Beam spot |
|---|---|---|---|---|---|
| Cr DCC, 75 w Cr tube | 0.05 sr. | 7 | 0.0035 | 5E9 | 300 μm |
| Mo DCC, 75 w Mo tube | 0.02 sr. | 10 | 0.002 | 8 E8 | 200 μm |

Figure 3A:
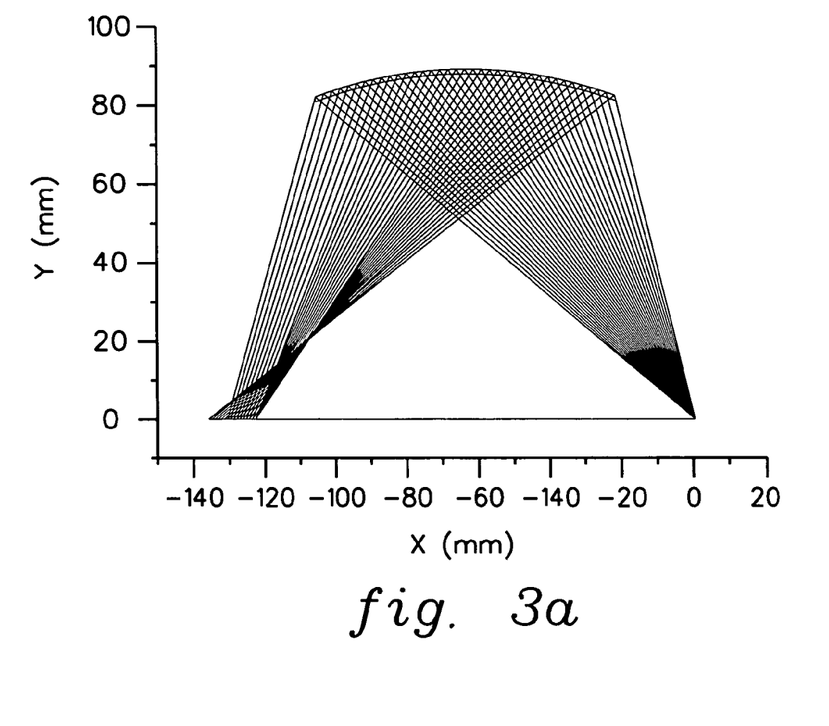
FIGS. 3a-c depict the geometry of a log spiral doubly curved crystal optic including: a) a log spiral curve, b) revolving log spiral profile and c) a photo of fabricated Ge(111) log spiral DCC for S K$\alpha$, containing 36 pieces of 10 mm×20 mm doubly curved crystals.
Figure 3B:
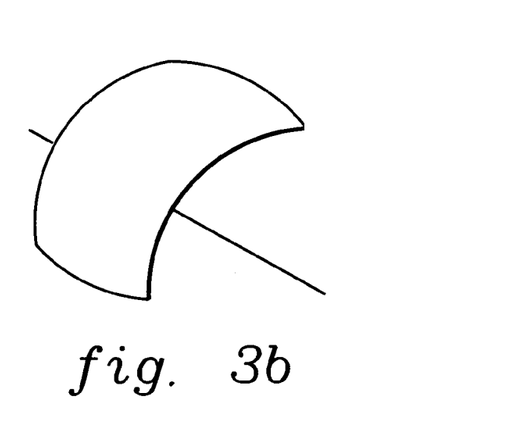
Figure 3C:
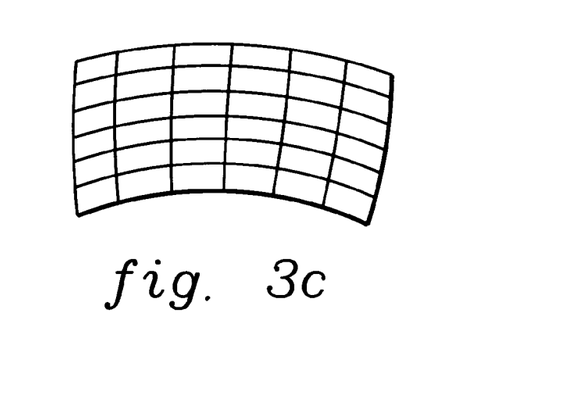

A doubly curved logarithmic spiral DCC optic (depicted generally in FIGS. 3*a-c*) was used for collecting sulfur x-rays emitted from a point. Log spiral DCC optics can provide a very large collection solid angle due to the fact that rays emitted from a log spiral origin form a constant angle over the entire curve. DCC log spiral geometry is obtained by rotating an optical axis passing through the origin.

Sulfur Detection Using WD-MXRF Technique

To measure low-levels of sulfur in fuel, a fixed channel wavelength dispersive monochromatic XRF system based on two DCC optics was proposed for the first time. See, e.g., X-Ray Optical Systems, Inc. U.S. Provisional Application 60/299,371 (filed Jun. 19, 2000 entitled XRF SYSTEM INCLUDING FOCUSING OPTIC ON EXCITATION SIDE AND MONOCHROMATIC COLLECTION and perfected as PCT Application PCT/US02/19272-W002/103710 entitled WAVELENGTH DISPERSIVE XRF SYSTEM USING FOCUSING OPTIC FOR EXCITATION AND A FOCUSING MONOCHROMATOR FOR COLLECTION) the entirety of which are incorporated herein by reference. As shown in FIG. 4, a compact analyzer 100 for measuring sulfur was designed based on the WD-MXRF concept using two DCCs 120 and 140 and a 75 w Cr tube 110. Due to the adsorption of both S Kα and Cr Kα x-rays in air, the two optics were enclosed in an evacuated chamber. The sample was placed outside of the chamber with a Be window that provides paths for both the excitation beam and emitted S Kα photons. A proportional counter 150 is used to detect the S Kα photons collected by the log spiral DCC 140.

The capability of the sulfur analyzer has been demonstrated. The linearity of the system was shown to be excellent from 0 to 3000 ppm. The minimum detection limits (MDL) of the system was determined by $$\text{MDL} = \frac{3\sqrt{B}}{S\sqrt{t}} W_i \quad (1)$$

where B is the background count rate in cps, S is the sensitivity in cps, t is the measurement time in seconds and $W_i$ is the weight concentration. For 300 s measurement time, the MDL is 0.2 ppm. For 1000 s measurement time, the MDL is 0.0 ppm. The detection limits achieved in this compact, sulfur analyzer is excellent and is much better than a high power (2 kW) WDS lab instrument.

Refinements of this approach are shown in further detail in X-Ray Optical Systems, Inc. U.S. Provisional Application Ser. No. 60/336,584 (filed Dec. 4, 2001 and entitled X-RAY TUBE AND METHOD AND APPARATUS FOR ANALYZING FLUID STREAMS USING X-RAYS, perfected as PCT Application PCT/US02/38792-W003/048745 entitled X-RAY TUBE AND METHOD AND APPARATUS FOR ANALYZING FLUID STREAMS USING X-RAYS)—the entirety of which are incorporated herein by reference.

Predicted Detection Limit for As

Based on the data from the sulfur analyzer, the detection capability for an As analyzer using the WD-MXRF technique can be predicted.

For As detection, a monochromatic Mo Kα beam will be used for As excitation. A Mo DCC for focusing Mo Kα x-rays and an As DCC for collecting As Kα photons will replace the Cr DCC and the S DCC. There are several differences between two systems. 1) The collection solid angle of the Mo DCC and As DCC will be smaller if the same design parameters are used, e.g, the same revolving angle. This is due to the fact that the collection solid angle is proportional to sin(Bragg angle) (Chen, Z. W. and Wittry D. W., "Microanalysis by Monochromatic Microprobe X-ray Fluorescence—Physical Basis, Properties and Future Prospects", J. Appl. Phys., 84 (2), 1064 (1998)—incorporated herein by reference in its entirety). Therefore, full revolving (360°) DCC optics (as shown in FIG. 1) may be needed to gain back the loss. With a large aperture DCC geometry, the collection solid angle can even be improved for the Mo excitation optic compared to the Cr DCC. Also the optical efficiency of the sulfur analyzer is low. Reflectivity of 15% can be achieved for a Mo DCC. For simplicity, we assume that the overall x-ray optical system of the As detection system can give approximately a factor of 2× improvement compared to the sulfur system. 2) The flux of the Mo Kα per unit solid angle from the tube will be lower compared to the same Cr Kα for the same setting (50 kv 1.5 mA) due to a decreased production yield of Mo Kα photons per electron on the anode (Green and Cosslett, "Measurement of K, L and M shell X-ray production efficiencies", Brit. J. Appl. Phys. (J. Phys. D), ser. 2, vol 1. p 425-436—incorporated by reference herein in its entirety). It is approximately a factor of 3 less. There was significant absorption loss of sulfur Kα signals in the beam path, including windows and air gap between the sample and the chamber. For the As system, there is no need for vacuum and the loss for As Kα x-rays in air can be assumed as 10% (for 300 mm air path). The window loss for As Kα will be insignificant.

Also the fundamental parameters related to x-ray fluorescence for As and S are different. These include the difference of photoelectric cross section and fluorescence yield as also listed in Table II. The fluorescence intensity is proportional to photoelectric cross section and fluorescence yield. The fluorescence yield for As K shell is about 8× higher than the S K shell. Finally the matrix effects are different. From the mass absorption coefficients, the escape depth and penetration depth for both systems can be calculated. For the sulfur system, the escaped depth of S Kα signal is about 0.075 mm (1/e distance) in fuel and the penetration depth of the Cr beam is about 1 mm. For the As system, the escape depth of As Kα in water is 2.3 mm and the penetration depth for Mo Kα is 10 mm. Since the signal is coming from a fraction of the excitation volume for both systems, the fluorescence intensity will be proportional to the escape depth.

Taking into account all the differences listed in Table II, the ratio of the As Kα intensity to S Kα intensity:

$$\frac{I_{As}}{I_S} = \frac{0.33 \times 2 \times 70 \times 0.59 \times 2.3 \times 0.9}{1 \times 1 \times 280 \times 0.076 \times 0.075 \times 0.5} = 71$$

TABLE II

Factors (in ab. units) to calculate the intensity ratio of sulfur signal and As signal

|  | Sulfur detection system | As detection System |
|---|---|---|
| Characteristic photon yield from the tube | 1 (Cr Kα) | ⅓~0.33 (Mo Kα) |
| Effective solid angle (solid angle × efficiency) | 1 | 2 |
| Photoelectric cross section | 280 | 70 |
| Fluorescence yields | 0.076 | 0.59 |
| Matrix effect, escape depth | 0.075 | 2.3 |
| Beam path transmission | 0.5 | 0.9 |

Therefore, the sensitivity for an As analyzer is about 71×0.8 cps/ppm, or 0.057 cps/ppb. To calculate the detection limits, an estimate for the background level for the As system is needed. As shown above, the background level of a sulfur analyzer was dominated by the S impurity in the Be window and the mylar film. For the As analyzer, there will be no Be window and the As trace in mylar film is much lower. It will be reasonable to assume that a background level of 0.03 cps is possible. For conservative reasons, we assume that the As analyzer will have a background level of 0.08 cps and sensitivity of about 0.05 cps/ppb. Then the minimum detection limits for As in water is by equation 1: (set Wi=10 ppb, S=0.5 cps).

$$\text{MDL} = \frac{3\sqrt{B}}{S\sqrt{t}} W_i = \frac{3 \times \sqrt{0.05}}{0.5 \times \sqrt{t}} \times 10 \text{ ppb} = \frac{17}{\sqrt{t}} \text{ ppb} \quad (2)$$

Figure 5:
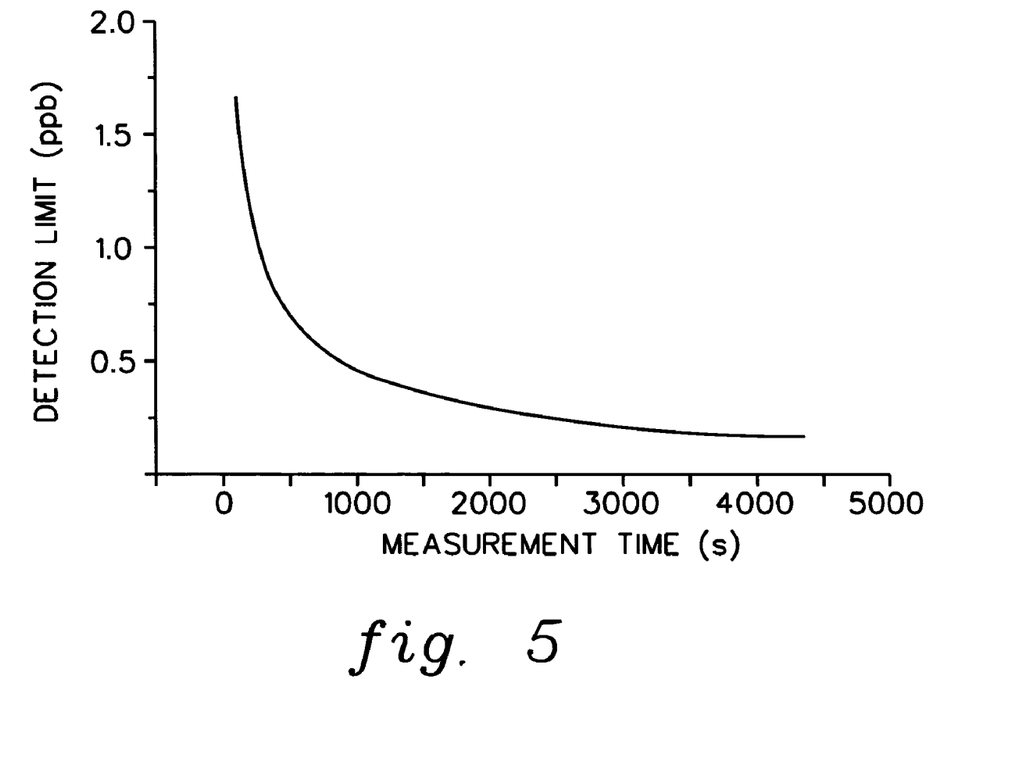
FIG. 5 depicts predicted detection limits for As in water analysis using WD-MXRF method.

The predicted minimum detection limit for As in water vs. measurement time t (in seconds) plotted is shown in FIG. 5. For 300 s measurement time, MDL=1 ppb. For 1000 s measurement time, MDL=0.5 ppb. This predicted minimum detection limit is excellent and it will meet the requirement for As measurement in drinking water. To achieve this MDL, we need to have a system with sensitivity better than 0.05 cps/ppb and a background level less than 0.05 cps. There are two keys for achieving these specifications: 1) an improvement factor of 2× for the optical system design and 2) to minimize the background of the As analyzer.

System Design:

Potential System Implementations

Figure 6A:
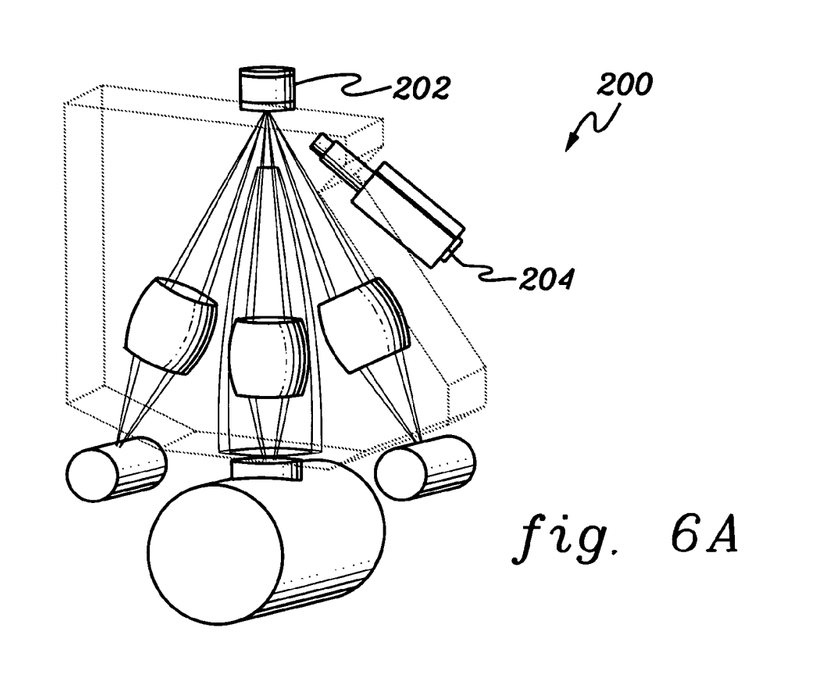
FIGS. 6a-b are schematic designs for an As analyzer for: a) portable in-field application and b) on-line continuously monitoring, in accordance with the present invention.
Figure 6B:
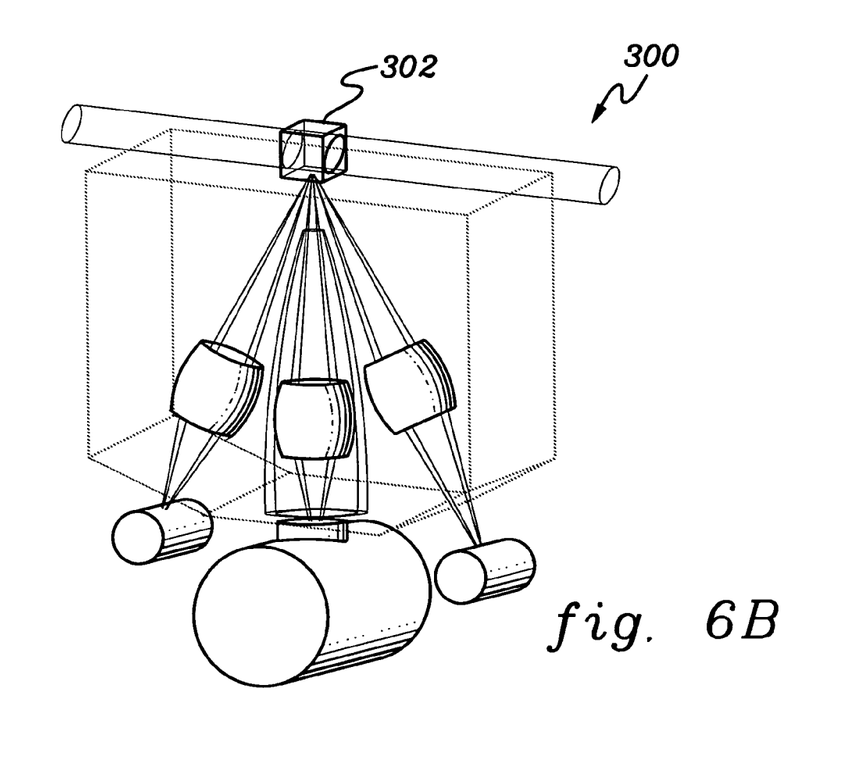

System configurations for in field and on-line applications are shown in FIGS. 6a-b, which in most respects are similar to system 10 of FIG. 1. For in field measurement, the analyzer 200 of FIG. 6a can be portable with a total power of less than 100 w. Proportional counters can be used to detect As and Pb photons from the collection DCCs. Power supplies can be used for detector biases and the x-ray tube. A small PLC can be used to control the system. A plastic cup 202 with thin plastic film can be used for water samples. Again, an ED detector 204 is an option for general multi-elemental analysis at higher concentration (ppm and sub ppm level).

For on-line continuous monitoring, a water stream delivery system 300 can be used (FIG. 6b), with otherwise similar components as in FIG. 6a. The ED detector may not be needed for the on-line design. A more robust window can be used in the sample cell 302.

Advanced Optics

Figure 7A:
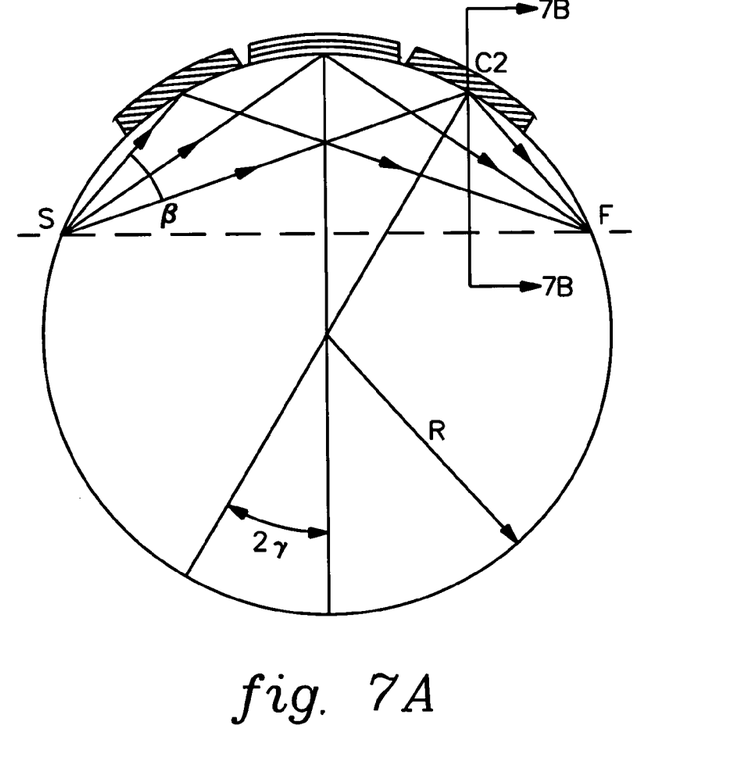
FIGS. 7a-b depict the geometry of a point focusing DCC using multiple crystals with different surface inclined angle for the diffraction planes.
Figure 7B:
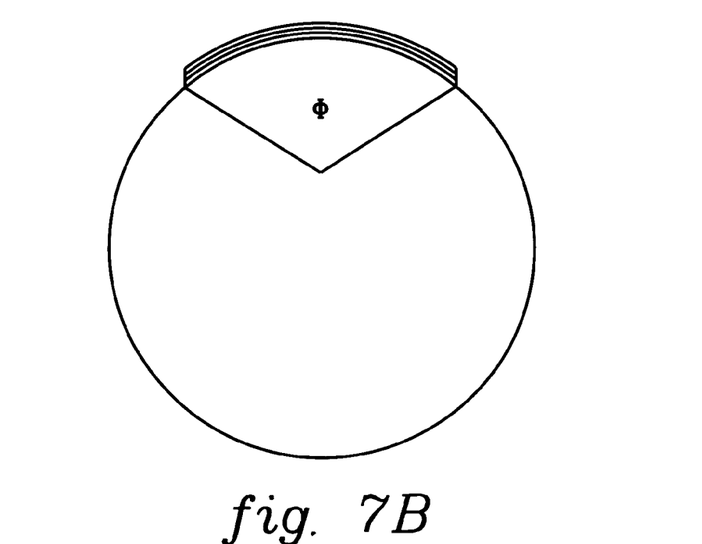

Designing doubly curved crystal optics with large collection solid angle is one of the keys to obtaining high sensitivity. A novel geometry, is shown in FIGS. 7a-b, for the excitation DCC (some aspects of which are disclosed in the above incorporated U.S. patent application entitled AN OPTICAL DEVICE FOR DIRECTING X-RAYS HAVING A PLURALITY OF OPTICAL CRYSTALS). In this geometry, multiple crystals curved to a radius of 2R (R is the radius of the focal circle) in the plane of the focal circle are tangential to the focal circle. The angle between the diffraction planes of each crystal and its surface is dependent on its location on the focal circle. For instance, the diffraction planes of the center crystal are parallel to its surface, which is the typical Johann geometry. The diffraction planes of crystal c2 have the inclined angle of γ relative to its surface. Each crystal is also curved in the transverse direction and they have rotation symmetry along line SF and the included rotation angle is φ. The collection angle in the plane focal circle is β. The collection solid angle of this geometry is given by $$\Omega = \phi(\cos(\theta_B - \beta/2) - \cos(\theta_B + \beta/2)) \quad (3)$$

where is $\theta_B$ the Bragg angle. The maximum value of φ is 2π, which is a full rotational DCC. The β value is dependent on the number of crystals used and the Bragg angle.

For excitation of As, Mo Kα x-rays is an obvious choice since Mo anode tubes are standard. Mo Kα photons are close to the absorption edge of As K shell excitation energy, but not too close to have Compton scattering background under the As peak. Either Si(220) and InSb(220) is proposed as a crystal diffraction plane for Mo Kα x-rays. Compared to Si(220) crystal, the reflectivity of InSb is higher since it has high atomic scattering factor due to its high atomic number. But the InSb is more brittle than Si.

Overall, because of the increased reflectivity and decreased absorption, the improvement of the As analyzer optical system leads to sub ppb detection capability of the As analyzer.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

What is claimed is:

1. An x-ray fluorescence apparatus for detecting the level of a specified material in a sample, wherein the specified material and an interference material are expected to fluoresce in a first energy band and the interference material is expected to also fluoresce separately in a second energy band, the apparatus comprising:
    an excitation path for directing x-rays toward the sample;
    a first detection path having a first detector for detecting x-ray fluorescence of the first energy band from the sample; and
    a second detection path having a second detector for detecting x-ray fluorescence of the second energy band from the sample;
    wherein the level of the specified material is obtained by analyzing the x-ray fluorescence from both detection paths, and using a constant which relates the level of the interference material in the second energy band to the level of interference material in the first energy band thereby providing the level of the specified material in the first energy band.

2. The apparatus of claim 1, wherein at least one of the detection paths includes a monochromating optic adapted to transmit energy from the respective energy band.

3. The apparatus of claim 2, wherein the monochromating optic comprises a doubly curved crystal optic.

4. The apparatus of claim 1, wherein the excitation path includes an excitation optic for focusing the x-rays onto the sample.

5. The apparatus of claim 4, wherein the excitation optic is a monochromating optic adapted to transmit x-rays of both the first and second energy bands.

6. The apparatus of claim 5, wherein the detection paths each include a monochromating optic adapted to transmit energy from the respective energy band.

7. The apparatus of claim 6, wherein the monochromating optics each comprises a doubly curved crystal optic.

8. The apparatus of claim 1, wherein the sample is a continuous stream or a static sample.

9. The apparatus of claim 1, wherein the specified material is arsenic, the interference material is lead, and the sample is water or body fluid.

10. The apparatus of claim 1, wherein the excitation path and each detection path includes a monochromating optic to transmit the desired x-ray energy band.

11. A method for detecting the level of a specified material in a sample, wherein the specified material and an interference material are expected to fluoresce in a first energy band and the interference material is expected to also fluoresce separately in a second energy band, the method comprising:
    directing x-rays toward the sample in an excitation path;
    detecting x-ray fluorescence of the first energy band from the sample in a first detection path having a first detector;
    detecting x-ray fluorescence of the second energy band from the sample in a second detection path having a second detector; and
    analyzing the x-ray fluorescence from both detection paths, using a constant which relates the level of the interference material in the second energy band to the level of interference material in the first energy band thereby providing the level of the specified material in the first energy band.

12. The method of claim 11, wherein at least one of the detection paths includes a monochromating optic adapted to transmit energy from the respective energy band.

13. The method of claim 12, wherein the monochromating optic comprises a doubly curved crystal optic.

14. The method of claim 11, wherein the excitation path includes an excitation optic for focusing the x-rays onto the sample.

15. The method of claim 14, wherein the excitation optic is a monochromating optic adapted to transmit x-rays of both the first and second energy bands.

16. The method of claim 15, wherein the detection paths each include a monochromating optic adapted to transmit energy from the respective energy band.

17. The method of claim 16, wherein the monochromating optics each comprises a doubly curved crystal optic.

18. The method of claim 11, wherein the sample is a continuous stream or a static sample.

19. The method of claim 11, wherein the specified material is arsenic, the interference material is lead, and the sample is water or body fluid.

20. The method of claim 11, wherein the excitation path and each detection path includes a monochromating optic to transmit the desired x-ray energy band.

21. An x-ray fluorescence apparatus for detecting the level of arsenic in a sample of water or body fluid, wherein arsenic and lead are expected to fluoresce in a first energy band and lead is expected to also fluoresce separately in a second energy band, the apparatus comprising:
   an excitation path for directing x-rays toward the sample;
   a first detection path having a first detector for detecting x-ray fluorescence of the first energy band from the sample; and
   a second detection path having a second detector for detecting x-ray fluorescence of the second energy band from the sample;
   wherein the level of arsenic is obtained by analyzing the x-ray fluorescence from both detection paths, and using a constant which relates the level of lead in the second energy band to the level of lead in the first energy band thereby providing the level of arsenic in the first energy band.

22. The apparatus of claim 21, wherein at least one of the detection paths includes a monochromating optic adapted to transmit energy from the respective energy band.

23. The apparatus of claim 22, wherein the monochromating optic comprises a doubly curved crystal optic.

24. The apparatus of claim 21, wherein the excitation path includes an excitation optic for focusing the x-rays onto the sample.

25. The apparatus of claim 24, wherein the excitation optic is a monochromating optic adapted to transmit x-rays of both the first and second energy bands.

26. The apparatus of claim 21, wherein the sample is a continuous stream or a static sample.

27. The apparatus of claim 26 wherein the apparatus is portable, for in-field use.

* * * * *

UNITED STATES PATENT AND TRADEMARK OFFICE
CERTIFICATE OF CORRECTION

PATENT NO. : 7,298,817 B2  Page 1 of 1
APPLICATION NO. : 11/000535
DATED : November 20, 2007
INVENTOR(S) : Chen et al.

It is certified that error appears in the above-identified patent and that said Letters Patent is hereby corrected as shown below:

In The Claims:

Claim 12, column 12, line 66: delete "monocbromating" and insert --monochromating--

Signed and Sealed this

Fifteenth Day of April, 2008

JON W. DUDAS
*Director of the United States Patent and Trademark Office*